(12) United States Patent
Tamura et al.

(10) Patent No.: US 11,147,439 B2
(45) Date of Patent: Oct. 19, 2021

(54) ENDOSCOPE LIGHT SOURCE DEVICE AND ENDOSCOPE SYSTEM

(71) Applicant: OLYMPUS CORPORATION, Tokyo (JP)

(72) Inventors: Kazuaki Tamura, Hachioji (JP); Masahiro Nishio, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 758 days.

(21) Appl. No.: 15/388,405

(22) Filed: Dec. 22, 2016

(65) Prior Publication Data

US 2017/0100021 A1    Apr. 13, 2017

Related U.S. Application Data

(63) Continuation of application No. PCT/JP2015/064961, filed on May 25, 2015.

(30) Foreign Application Priority Data

Jun. 25, 2014    (JP) .............................. JP2014-130774

(51) Int. Cl.
*A61B 1/06*    (2006.01)
*A61B 1/00*    (2006.01)
*G02B 23/24*    (2006.01)

(52) U.S. Cl.
CPC ........ *A61B 1/0661* (2013.01); *A61B 1/00025* (2013.01); *A61B 1/06* (2013.01); *A61B 1/0638* (2013.01); *G02B 23/2476* (2013.01)

(58) Field of Classification Search
CPC ............. A61B 1/0661; A61B 1/00025; A61B 1/0638; A61B 1/06; A61B 1/00027;
(Continued)

(56) References Cited

U.S. PATENT DOCUMENTS 6,489,749 B1 *    12/2002    Nakashimo ........... H02J 7/0047
                                                320/134
2002/0137987 A1 *    9/2002    Watanabe .......... A61B 1/00105
                                                600/178
(Continued)

FOREIGN PATENT DOCUMENTS

JP    H04-285879 A    10/1992
JP    H06-21867 A    1/1994
(Continued)

OTHER PUBLICATIONS

Japanese Office Action dated Apr. 24, 2018 in Japanese Patent Application No. 2014-130774.
(Continued)

*Primary Examiner* — Timothy J Neal
*Assistant Examiner* — Genja M Frankert
(74) *Attorney, Agent, or Firm* — Scully, Scott, Murphy & Presser, P.C.

(57) ABSTRACT

A light source device includes a detector that detects a remaining capacity, and a prediction calculation circuit that calculates a capacity consumption predictive value indicating a ratio of consuming a capacity of a supply source within a predetermined period of time in each illumination mode. The light source device further includes a capability calculation circuit that calculates a driving capability of the supply source corresponding to each of the illumination modes, based on the remaining capacity and the capacity consumption predictive value; and a reporting unit that reports the driving capability.

16 Claims, 7 Drawing Sheets

(58) Field of Classification Search
CPC ............ A61B 1/00036; A61B 1/00034; A61B 2560/0204; A61B 2560/0214; A61B 1/041; G02B 23/2476; H02J 7/007; H02J 7/041; H02J 7/0073; H02J 2007/0049; H02J 2007/005; H01M 2010/4271
See application file for complete search history.

(56) References Cited

U.S. PATENT DOCUMENTS

| | | | | |
|---|---|---|---|---|
| 2003/0060682 | A1* | 3/2003 | Handa | A61B 1/0669 600/178 |
| 2006/0155166 | A1* | 7/2006 | Takahashi | A61B 1/045 600/109 |
| 2006/0220614 | A1* | 10/2006 | Abe | A61B 1/00016 320/114 |
| 2007/0066868 | A1* | 3/2007 | Shikii | A61B 1/00036 600/118 |
| 2007/0232887 | A1* | 10/2007 | Bettesh | A61B 1/041 600/407 |
| 2008/0262299 | A1* | 10/2008 | Niida | A61B 1/05 600/110 |
| 2010/0259656 | A1* | 10/2010 | Irion | A61B 1/00186 348/273 |
| 2011/0068941 | A1* | 3/2011 | Nunomaki | H01M 10/48 340/636.1 |
| 2012/0271104 | A1* | 10/2012 | Khait | A61B 1/041 600/109 |
| 2015/0099932 | A1* | 4/2015 | Morimoto | H05B 33/0854 600/180 |
| 2015/0182106 | A1* | 7/2015 | King | A61B 1/043 600/431 |
| 2015/0182107 | A1* | 7/2015 | King | A61B 1/05 600/473 |
| 2017/0014021 | A1* | 1/2017 | Kuramoto | A61B 1/0669 |

FOREIGN PATENT DOCUMENTS

| | | |
|---|---|---|
| JP | 2001-218737 A | 8/2001 |
| JP | 2002-102142 A | 4/2002 |
| JP | 2004-048986 A | 2/2004 |
| JP | 2004-298353 A | 10/2004 |
| JP | 2005-237430 A | 9/2005 |
| JP | 2006-280542 A | 10/2006 |
| JP | 2007-252686 A | 10/2007 |
| JP | 2008-078009 A | 4/2008 |
| JP | 2012-105715 A | 6/2012 |
| WO | WO 2005/071372 A1 | 8/2005 |

OTHER PUBLICATIONS

Chinese Office Action dated Sep. 30, 2017 in Chinese Patent Application No. 201580034083.9.
Japanese Office Action dated Oct. 9, 2018 in Japanese Patent Application No. 2014-130774.
Japanese Office Action dated Apr. 2, 2019 in Japanese Patent Application No. 2014-130774.
English translation of International Preliminary Report on Patentability dated Jan. 5, 2017 together with the Written Opinion received in related International Application No. PCT/JP2015/064961.
International Search Report dated Aug. 18, 2015 issued in PCT/JP2015/064961.

* cited by examiner

ENDOSCOPE LIGHT SOURCE DEVICE AND ENDOSCOPE SYSTEM

CROSS-REFERENCE TO RELATED APPLICATIONS

This application is a Continuation Application of PCT Application No. PCT/JP2015/064961, filed May 25, 2015 and based upon and claiming the benefit of priority from prior Japanese Patent Application No. 2014-130774, filed Jun. 25, 2014, the entire contents of all of which are incorporated herein by reference.

BACKGROUND OF THE INVENTION

1. Field of the Invention

The present invention relates to an endoscope light source device and an endoscope system.

2. Description of the Related Art

Recently, an illuminating apparatus that switches a destination of supplying energy, for example, electric power, to one of a plurality of light sources from a supply source such as a battery, and an illuminating apparatus that is applied to an endoscope, have been developed.

For example, Jpn. Pat. Appln. KOKAI Publication No. 2008-78009 discloses an illuminating apparatus that is capable of switching connection between a supply source and one of two light sources. In this illuminating apparatus, if a voltage of the supply source reaches a predetermined value or lower while the supply source is connected to one of the light sources, the connection is switched, the supply source supply electric power to another light source that is connected the another light source.

For example, Jpn. Pat. Appln. KOKAI Publication No. 2007-252686 discloses an endoscope apparatus in which a plurality of units each having a supply source and a light source are disposed. If a voltage of a supply source reaches a predetermined value or lower during supplying power in one of the units, the supply source is disconnected to the light source. Then, the supply source is connected to the light source in the other unit to supply electric power to the light source. In this example, the connection is switched for each unit.

BRIEF SUMMARY OF THE INVENTION

An aspect of an endoscope light source device of the invention is an endoscope light source device that is driven by energy supplied from a supply source, and is operable by switching between a plurality of illumination modes, the device includes; a detector that detects a remaining capacity of the supply source; a prediction calculation circuit that calculates a capacity consumption predictive value indicating a ratio of consuming a capacity of the supply source within a predetermined period of time in each illumination mode, based on required consumption energy information that indicates a consumption energy amount required for driving each illumination mode; a capability calculation circuit that calculates a driving capability of the supply source corresponding to each of the illumination modes, based on the remaining capacity and the capacity consumption predictive value; and a reporting unit, including at least one of a display and a transmitter, that reports the driving capability.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute apart of the specification, illustrate embodiments of the invention, and together with the general description given above and the detailed description of the embodiments given below, serve to explain the principles of the invention.

DETAILED DESCRIPTION OF THE INVENTION

Figure 1:
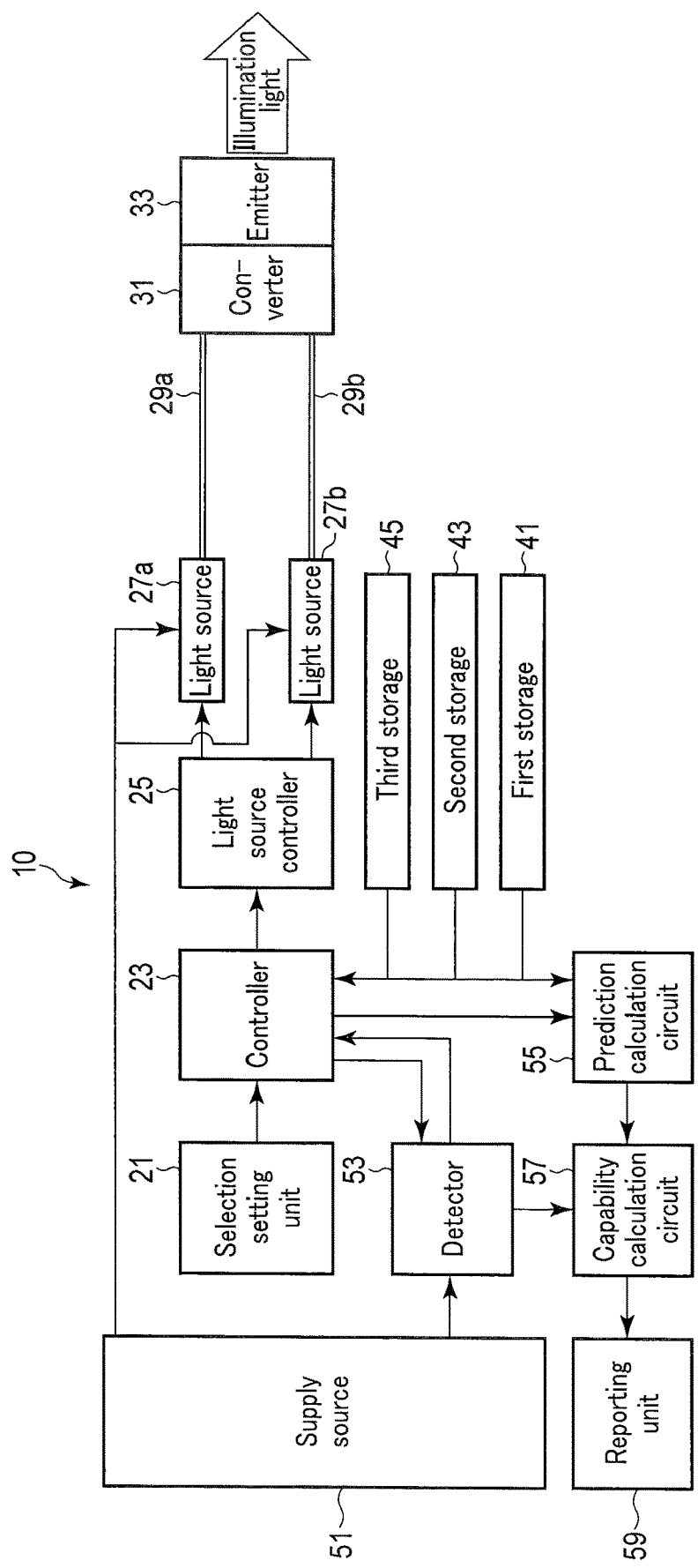
FIG. 1 is a schematic diagram of an endoscope light source device according to a first embodiment of the present invention.

Hereinafter, embodiments of the present invention will be described with reference to the drawings. Some elements in some of the drawings will be omitted for simplification.

First Embodiment

Configuration

A first embodiment will be described with reference to FIG. 1, FIG. 2A, FIG. 2B, FIG. 3A, FIG. 3B, FIG. 4 and FIG. 5.

Each element of the endoscope light source device 10 (hereinafter referred to as a light source device 10) will be explained with reference to FIG. 1. The light source device 10 having elements is driven by energy (for example, electric power) supplied from a supply source 51 described later. Each element of the light source device 10 is disposed at a suitable predetermined position of an endoscope not shown in the drawings. Each element may be disposed at a suitable predetermined position of a peripheral device connected to the endoscope not shown in the drawings.

As shown in FIG. 1, in the present embodiment, the light source device 10 includes a plurality of light sources 27a and 27b, an illumination mode using a light emitted from the light source 27a is referred to as a first illumination mode, and an illumination mode using a light emitted from the light source 27b is referred to as a second illumination mode. The light source device 10 is operable by switching between the illumination modes. The number of light sources is not limited to two, and may be two or more.

As shown in FIG. 1, the light source device 10 includes a selection setting unit 21 that selects and sets the illumination mode, a controller (control unit) 23 that switches to the illumination mode selected and set by the selection setting unit 21, and a light source controller (light source control unit) 25 that controls the light source 27a or 27b corresponding to the illumination mode switched by the controller 23. The controller 23 and the light source controller 25 include an electronic circuit such as a CPU or an ASIC, or a processor included in hardware. The plurality of light sources 27a and 27b are controlled by the light source controller 25 to emit the light corresponding to an illumination mode. The light source device 10 includes light guide members 29a and 29b that guide the light emitted from the light sources 27a and 27b. The light source device 10 further includes a converter (conversion unit) 31 that converts the light guided by the light guide members 29a and 29b to an illumination light, and an emitter (emission portion) 33 that externally emits the illumination light.

The selection setting unit 21 can adjust and set a light amount, for example, in the illumination mode. The selection setting unit 21 has a button, for example, for selection, setting, and adjustment. The selection setting unit 21 is operated by a user.

When the selection setting unit 21 selects and sets the illumination mode, the controller 23 refers to a driving state and a driving condition corresponding to the illumination mode, and controls the light source controller 25 based on the driving state and the driving condition. The driving state and the driving condition are stored in a third storage (third storage unit) 45 described later. The controller 23 controls the light amount in the illumination mode adjusted by the selection setting unit 21.

The light source controller 25 controls the light sources 27a and 27b based on a control of the controller 23. In the present embodiment, for example, the light source controller 25 controls the energy to be supplied to the light sources 27a and 27b in accordance with the illumination mode, in the other word, the light source controller 25 switches a destination of the energy supply in accordance with the illumination mode. Accordingly, the light sources 27a and 27b are independently driven in accordance with the illumination mode. Each illumination mode emit the illumination light having a different light emission spectrum by the control of the light source controller 25. The light source controller 25 controls the amount of the energy to be supplied by controlling at least two different types of driving currents. By this operation, the light amount varies for each illumination mode, for example, as a maximum light amount state, an electric power save state, and an average light amount state, described below.

The light sources 27a and 27b emit light each having a desired light emission peak intensity in different wavelength regions each other. The light source 27a emits light having a desired light emission peak intensity in a first wavelength region, for example. The light source 27b emits light having a desired light emission peak intensity in a second wavelength region which is different from the first wavelength region, for example.

Figure 2A:
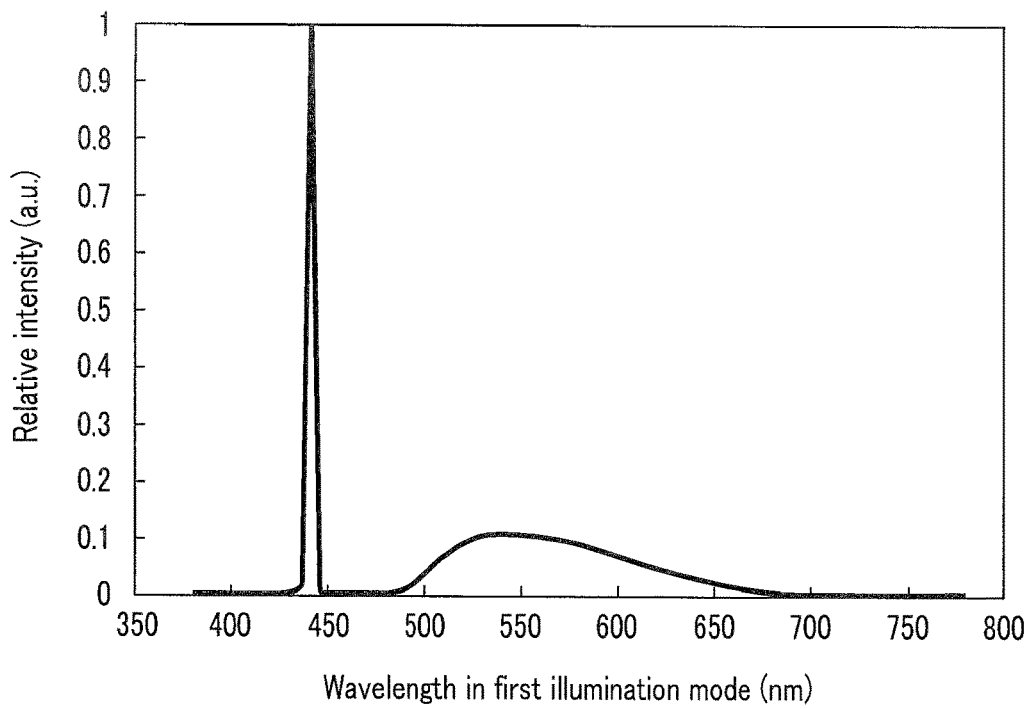
FIG. 2A illustrates a light emission peak intensity in a first illumination mode.

As shown in FIG. 2A, the light source 27a has a semiconductor laser that emits a blue laser beam in which a wavelength peak is 445 nm, for example.

Figure 2B:
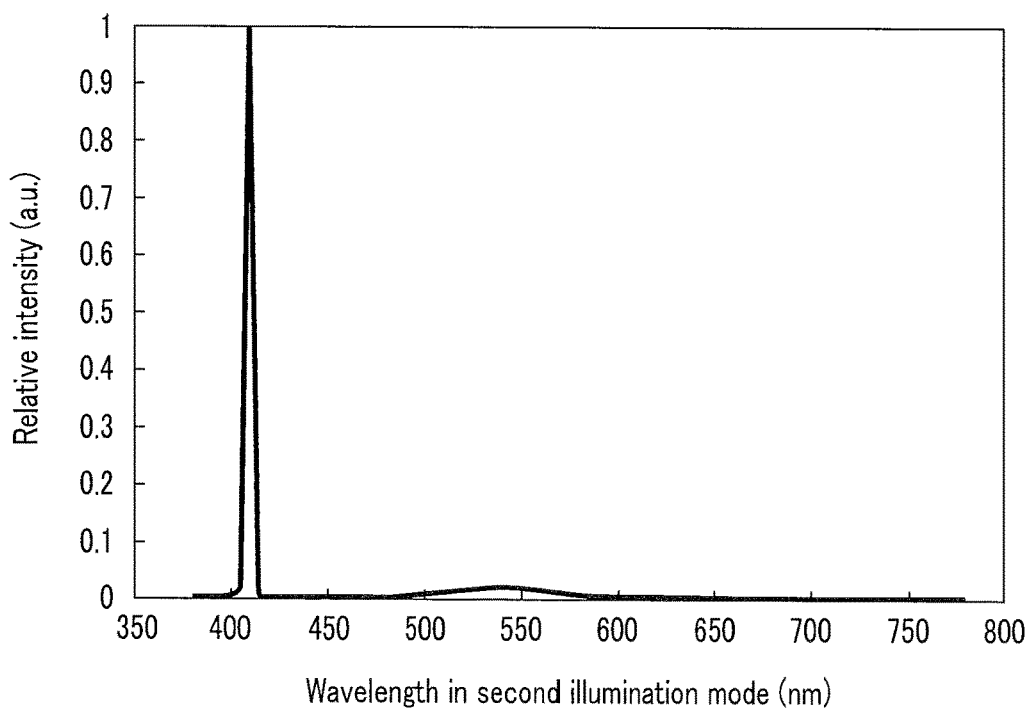
FIG. 2B illustrates a light emission peak intensity in a second illumination mode.

As shown in FIG. 2B, the light source 27b has a semiconductor laser that emits a violet laser beam in which the wavelength peak is 405 nm, for example.

The light sources 27a and 27b each have a thermal radiation member not shown in the drawings that radiates heat generated from the light sources 27a and 27b when the light sources 27a and 27b emit the light. The thermal radiation member includes, for example, a heat sink or a Peltier device. The light source controller 25 supplies the electric power required for driving the thermal radiation member, and the thermal radiation member is controlled by the light source controller 25.

The light sources 27a and 27b may have a semiconductor laser that combines multiple light each having a desired light emission peak intensity in different wavelength regions and emits the combined light.

The light guide members 29a and 29b have an optical fiber, for example. The optical fiber has the core diameter of 50 μm, and the numerical aperture FNA is 0.2, for example. The optical fiber is a fiber for multiple modes.

The converter 31 converts optical properties of the light guided by the light guide members 29a and 29b, and generates the illumination light.

The converter 31 has a wavelength conversion member that generates a yellow fluorescence from the blue laser beam by absorbing a blue wavelength, and converting the blue wavelength to a yellow wavelength. Such a wavelength conversion member has a YAG phosphor, for example. The YAG phosphor has optical properties in that a violet wavelength is not absorbed, but the violet laser beam is allowed to pass through.

The converter 31 has a wavelength conversion member that generates a green fluorescence from the violet laser beam by absorbing the violet wavelength, and converting the violet wavelength to a green wavelength to generate a green fluorescence from the violet laser beam. Such a wavelength conversion member has a sialon phosphor, for example.

In the present embodiment, mixed light, in which the blue laser beam and the yellow fluorescence generated by the converter 31 are mixed and generated when the light source 27a that emits the blue laser beam is driven, is referred to as a first illumination light. An illumination mode in which the first illumination light is used is referred to as the first illumination mode. In this case, the mixed light is white.

In the present embodiment, mixed light, in which the violet laser beam and the green fluorescence generated by the converter 31 are mixed and generated when the light source 27b that emits the violet laser beam is driven, is referred to as a second illumination light. An illumination mode in which the second illumination light is used is referred to as the second illumination mode.

The first illumination mode has, for example, the maximum light amount state, the electric power save state, and the average light amount state. In the maximum light amount state, the light amount of the first illumination light is maximum among the three states. In the electric power save state, the light amount of the first illumination light is minimum, but does not adversely affect observation processing. In the average light amount state, the light amount of the first illumination light is an average value of that in the maximum light amount state and the electric power save state. The state is selected by the selection setting unit 21. The second illumination mode also has the states similar to those explained for the first illumination mode.

As shown in FIG. 1, the light source device 10 includes a first storage 41 (first storage unit), a second storage 43 (second storage unit), and the third storage 45.

Figure 3A:
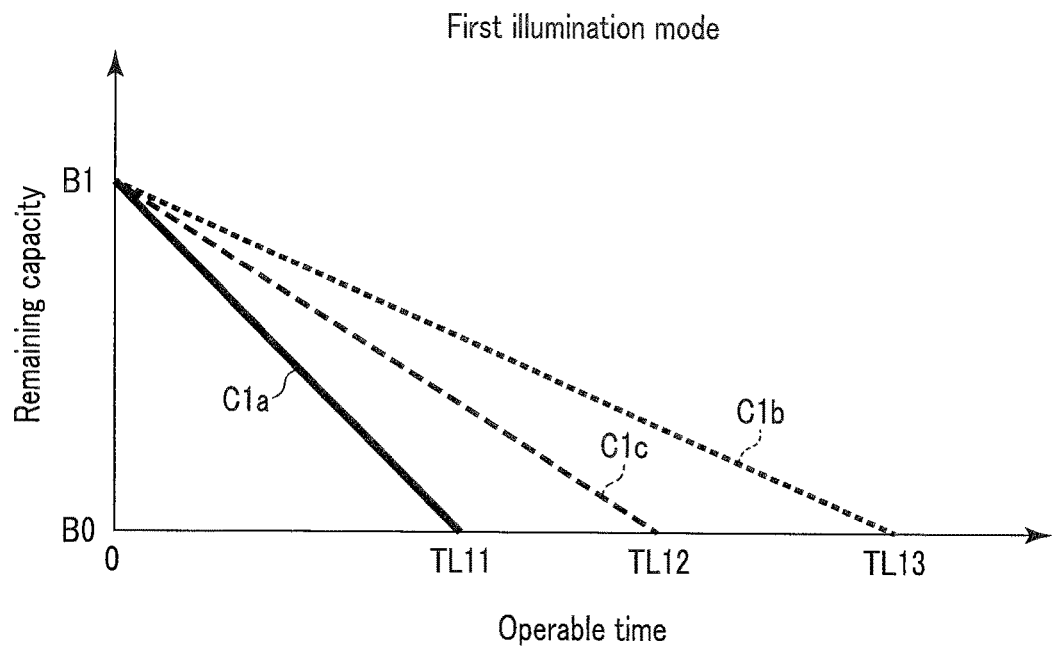
FIG. 3A illustrates a relationship between a remaining capacity of a supply source and an operable time in each state of the first illumination mode, and shows a concept of energy capacity consumption in each state of the first illumination mode.
Figure 3B:
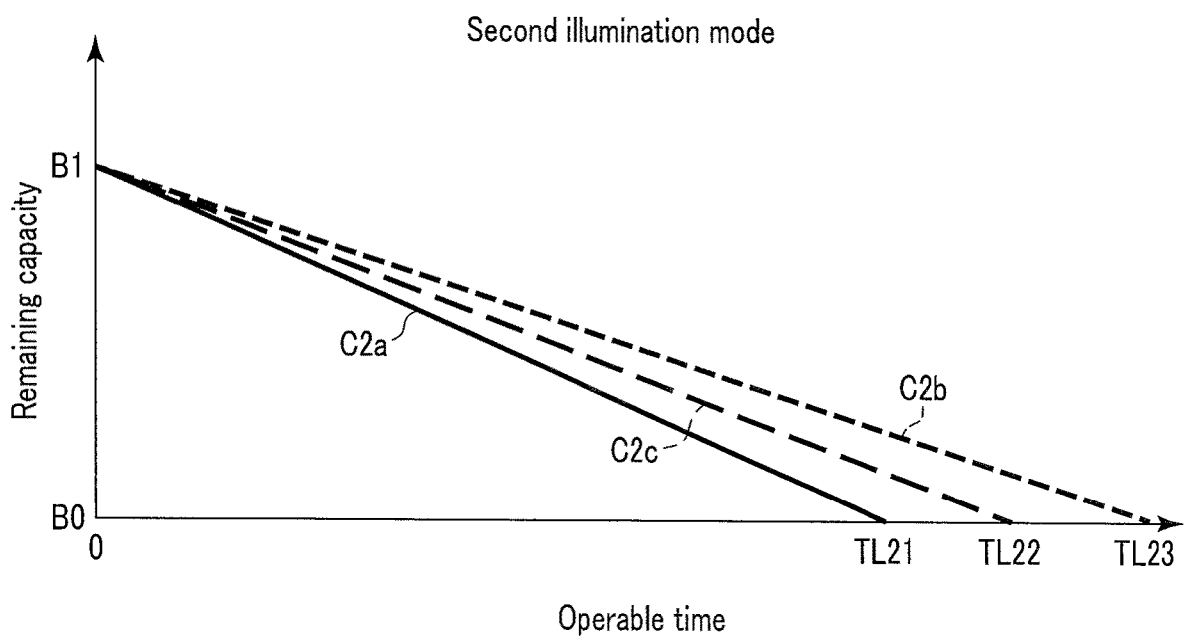
FIG. 3B illustrates a relationship between a remaining capacity of a supply source and an operable time in each state of the second illumination mode, and shows a concept of energy capacity consumption in each state of the second illumination mode.

The first storage 41 stores required consumption energy information indicating the consumption energy amount required for driving each illumination mode. The required consumption energy information includes a consumption electric power amount indicating the electric power to be consumed in each illumination mode. As shown in FIGS. 3A and 3B, the consumption electric energy amount includes coefficients C1$a$ and C2$a$ in the maximum light amount state, coefficients C1$b$ and C2$b$ in the electric power save state, and coefficients C1$c$ and C2$c$ in the average light amount state in each illumination mode. The coefficients C1$a$, C1$b$, and C1$c$ are coefficients in each state for the first illumination mode. The coefficients C2$a$, C2$b$, and C2$c$ are coefficients in each state for the second illumination mode. These coefficients are preferably predetermined, and indicated as inclinations in FIGS. 3A and 3B.

As shown in FIGS. 3A and 3B, coefficients C1$a$ and C2$a$ in the maximum light amount state are highest, coefficients C1$b$ and C2$b$ in the electric power save state are lowest, and coefficients C1$c$ and C2$c$ in the average light amount state show average values of the coefficients C1$a$ and C2$a$ in the maximum light amount state, and the coefficients C1$b$ and C2$b$ in the electric power save state.

For example, the operable time is TL11 for the remaining capacity B1 and the coefficient C1$a$, the operable time is TL13 for the remaining capacity B1 and the coefficient C1$b$, the operable time is TL12 for the remaining capacity B1 and the coefficient C1$c$, and the operable time is reduced in order from TL13 to TL12 to TL11. For example, the operable time is TL21 for the remaining capacity B1 and the coefficient C2$a$, the operable time is TL23 for the remaining capacity B1 and the coefficient C2$b$, the operable time is TL22 for the remaining capacity B1 and the coefficient C2$c$, and the operable time is reduced in order from TL23 to TL 22 to TL21.

The coefficient C1$a$ in the maximum light amount state for the first illumination mode may be the same as or different from the coefficient C2$a$ in the maximum light amount state for the second illumination mode. This feature is the same for the electric power save state and the average light amount state.

The first storage 41 stores energy capacity consumption information indicating the ratio of consuming the capacity of the supply source 51 by energy for each illumination mode.

Specifically, as shown in FIG. 3A, the energy capacity consumption information indicates, for example, how much time the maximum light amount state of the first illumination mode can operate while the remaining capacity B1 of the supply source 51 decreases to the remaining capacity B0. More specifically, the energy capacity consumption information indicates, for example, an operable time in the maximum light amount state for the first illumination mode.

The remaining capacity B1 indicates a full capacity (full charge) state or a predetermined remaining capacity. The remaining capacity B0 indicates a state where the remaining capacity becomes zero, or the allowable lower limit where the maximum light amount state is operable. In this case, the operable time in the maximum light amount state for the first illumination mode is calculated by the controller 23 based on the remaining capacities B1, B0, and the coefficient C1$a$ stored in the first storage 41 beforehand, and stored in the first storage 41.

The above is also applicable to the electric power save state and the average light amount state for the second illumination mode as shown in FIG. 3A, and the maximum light amount state, the electric power save state, and the average light amount state for the second illumination mode as shown in FIG. 3B.

The second storage 43 stores the illumination mode selected and set by the selection setting unit 21, and each state of the illumination mode selected and set by the selection setting unit 21.

The second storage 43 also stores accumulated consumption energy information. The accumulated consumption energy information is obtained by associating the consumption energy information indicating the consumed energy in each illumination mode with the operable time for each illumination mode, and indicates the energy amount (electric power amount) which is the amount of accumulated actual consumed energy in each illumination mode.

The second storage 43 stores an initial value of the capacity of the supply source 51. The initial value includes a full capacity (full charge). The initial value is set by converting the capacity by the controller 23, based on a voltage value between terminals of the supply source 51 when the supply source 51 is at full capacity (fully charged). The initial value may be set by converting the capacity by the controller 23, based on a charging time and the number of times of charging of the supply source 51 and a corresponding voltage value between terminals.

The third storage 45 stores the driving state that indicates how to drive the light sources 27$a$ and 27$b$ for each illumination mode. The driving state indicates a destination of energy supply in independent driving controlled by the light source controller 25, for example, the driving state may indicate that the light source 27$a$ is driven in the first illumination mode, and the light source 27$b$ is driven in the second illumination mode. The third storage 45 also stores the driving conditions that indicates under what kind of conditions the light sources 27$a$ and 27$b$ are driven in each illumination mode. The driving condition indicates each state (maximum light amount state, electric power save state, and average light amount state) in the first illumination mode and the second illumination mode.

As shown in FIG. 1, the light source device 10 includes the supply source 51 that supplies energy to each element, and a detector (detection unit) 53 that detects the remaining capacity of the supply source 51.

As shown in FIG. 1, the light source device 10 further includes a prediction calculation circuit (prediction calculation unit)55 that calculates a capacity consumption predictive value indicating a ratio of consuming the capacity of the supply source 51 within a predetermined period of time in each illumination mode, based on the required consumption energy information that indicates the consumption energy amount required for driving each illumination mode stored in the first storage 41. The required consumption energy information indicates the electric power required for driving each illumination mode.

As shown in FIG. 1, the light source device 10 includes a capability calculation circuit (capability calculation unit) 57 that calculates a driving capability of the supply source 51 corresponding to each illumination mode, based on the remaining capacity detected by the detector 53 and the capacity consumption predictive value calculated by the prediction calculation circuit 55, and a reporting unit 59 that reports the driving capability.

The supply source 51 includes a battery that stores the electric power and supplies the electric power. The supply source 51 is chargeable by an external charger.

The detector 53 detects the remaining capacity at a predetermined timing or for a predetermined period of time based on a control instruction of the controller 23. For example, the detector 53 continuously detects the remaining capacity when the light source device 10 is driven. The predetermined timing is, for example, a time when the detector 53 receives the control instruction from the controller 23 in response to an input operation by the user at the selection setting unit 21. The predetermined period of time is, for example, a predetermined period from the time the detector 53 receives the control instruction. The timing and period of time are not particularly limited.

When detecting the remaining capacity, the detector 53 detects the remaining capacity based on the voltage value of the supply source 51 that varies in accordance with the change in the remaining capacity, for example. Otherwise, the detector 53 may detect the remaining capacity based on the accumulated consumption energy information stored in the second storage 43. In detail, the detector 53 detects a difference between the initial value of the capacity of the supply source 51 and the accumulated consumption energy information as the remaining capacity, for example.

The detector 53 transmits the remaining capacity which is a detection result to the controller 23 and the capability calculation circuit 57. If the controller 23 has determined that the remaining capacity is at a predetermined value or lower, the controller 23 may stop driving of the light source device 10, including the illumination modes.

Figure 4:
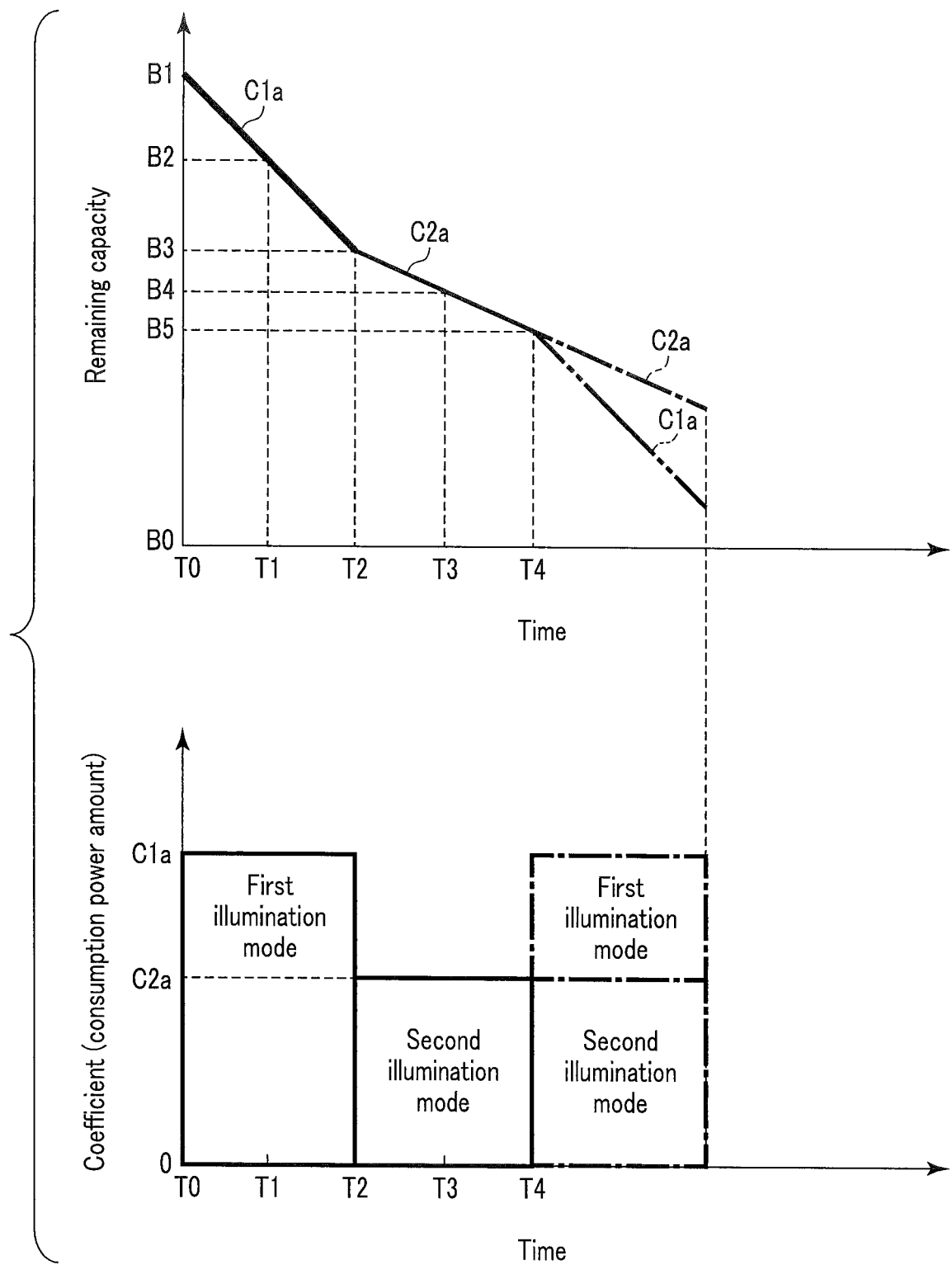
FIG. 4 illustrates a change in remaining capacity for each illumination mode over time, and the remaining capacity for each mode calculated at time T4 when each illumination mode is driven at a predetermined energy (electric power consumption).
Figure 5:
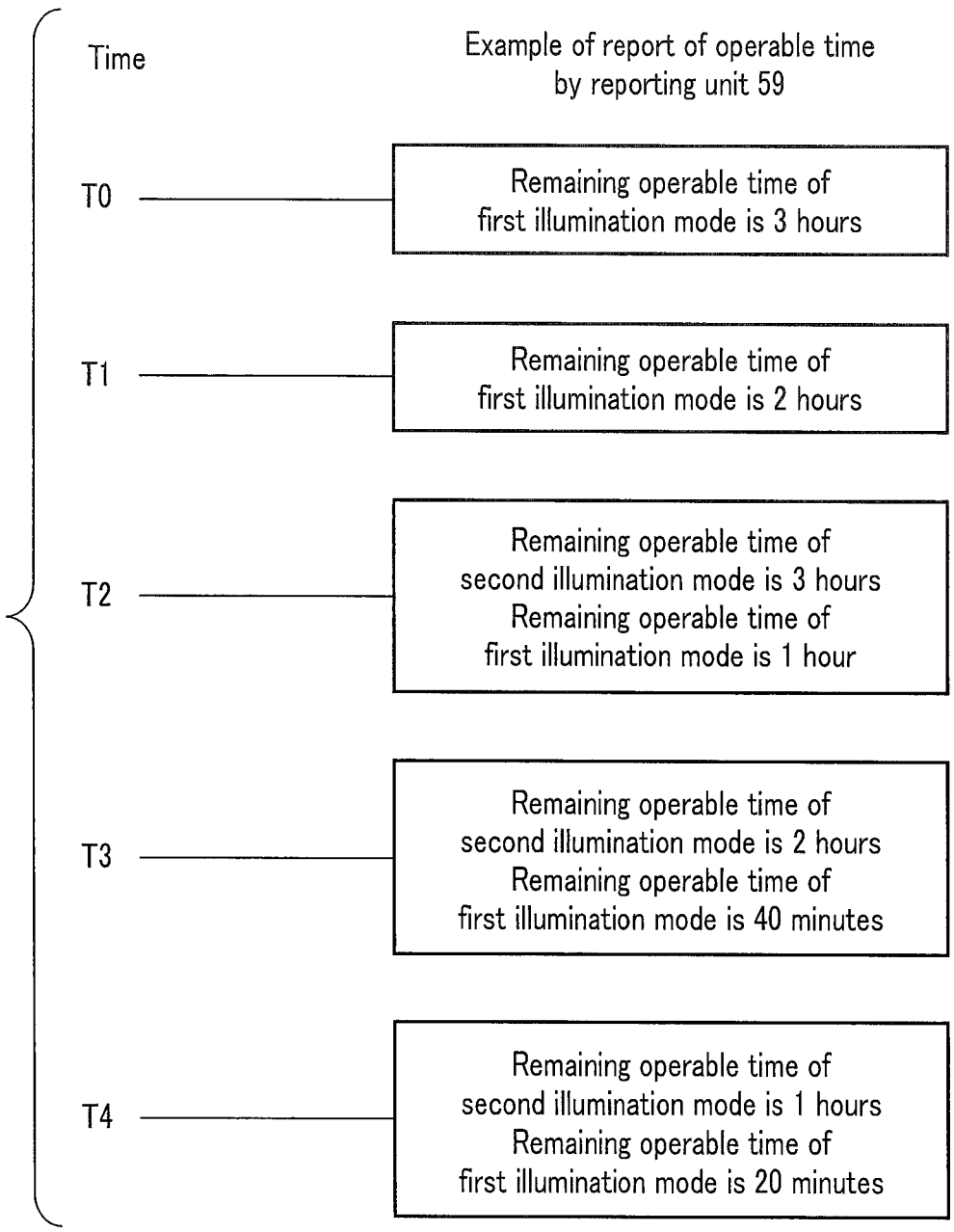
FIG. 5 illustrates an example of a report of an operable time for each illumination mode over time.

At the times T0 and T1 shown in FIGS. 4 and 5, while one of the illumination modes, e.g., the first illumination mode, is to be driven or is driven, the prediction calculation circuit 55 calculates the capacity consumption predictive value of the one of the illumination modes based on the required consumption energy information for the illumination mode.

It is assumed that the controller 23 switches from one of the illumination modes, e.g., the first illumination mode, to the other, e.g., the second illumination mode, in response to the operation of the selection setting unit 21, at the time T2 shown in FIGS. 4 and 5.

At the time T2 shown in FIGS. 4 and 5, when one of the illumination modes, e.g., the first illumination mode is switched to the other, e.g., the second illumination mode, the prediction calculation circuit 55 calculates the capacity consumption predictive value of the switched illumination mode.

At the times T2 and T3 shown in FIGS. 4 and 5, while the other one of the illumination modes, e.g., the second illumination mode, is to be driven or is driven, the prediction calculation circuit 55 calculates the capacity consumption predictive value of the other illumination mode based on the required consumption energy information for the other illumination mode which is different from the required consumption energy information for the one of the illumination modes. In this case, when one of the illumination modes which is the first illumination mode is switched to the other illumination mode which is the second illumination mode, the one of the illumination modes is not driven, and the other illumination mode is to be driven or is driven (see T2 and T3), the prediction calculation circuit 55 may calculate the capacity consumption predictive value of the one of the illumination modes by calculating the consumption energy information of the one of the illumination modes, based on the accumulated consumption energy information of the one of the illumination modes that indicates the energy amount that has been actually consumed in the first illumination mode. The accumulated consumption energy information is stored in the second storage 43, as described above. That is, the prediction calculation circuit 55 may calculate the driving capability of the supply source 51 corresponding to the first illumination mode which is an undriven illumination mode, based on the accumulated consumption energy information (capacity consumption predictive value).

Accordingly, the prediction calculation circuit 55 calculates the capacity consumption predictive value based on the required consumption energy information, the energy capacity consumption information stored in the first storage 41, and the accumulated consumption energy information stored in the second storage 43.

The prediction calculation circuit 55 transmits the calculated capacity consumption predictive value to the capability calculation circuit 57, as described above.

At time T4 shown in FIGS. 4 and 5, if the controller 23 has determined that the illumination mode is in a stand-by state, the capability calculation circuit 57 calculates the driving capability corresponding to each illumination mode. Then, the reporting unit 59 simultaneously reports the driving capability for each illumination mode.

In the capability calculation circuit 57, the driving capability of the supply source 51 has, for example, the operable time indicating that each illumination mode can be continuously used relative to the remaining capacity. In other words, the driving capability indicates the operable capability of the illumination mode with the remaining capacity of, for example, time. That is, the capability calculation circuit 57 calculates the operable time that each illumination mode is operable with the remaining capacity, based on the remaining capacity and the capacity consumption predictive value.

The capability calculation circuit 57 may calculate the ratio of the remaining capacity to the full capacity (full charge), based on the remaining capacity and the capacity consumption predictive value.

The detector 53, the prediction calculation circuit 55, and the capability calculation circuit 57 include an electronic circuit such as a CPU or an ASIC, or a processor included in hardware.

The reporting unit 59 reports the driving capability for each illumination mode. The reporting unit 59 includes at least one of a display (display portion) to display the driving capability such as time to the user, and a transmitter (transmit portion) to transmit the driving capability to the user. The display has a monitor, for example. The transmitter has a vibrator, for example. The reporting method of the reporting unit 59 is not particularly limited.

At the time T3 shown in FIGS. 4 and 5, when the first illumination mode which is one of the illumination modes is switched to the second illumination mode which is the other of the illumination modes, and the first illumination mode is not driven, and the second illumination mode is to be driven or is driven, the reporting unit 59 may report not only the driving capability of the supply source 51 corresponding to the second illumination mode which is driven and which is one of the illumination modes, but also the driving capability of the supply source 51 corresponding to the first illumination mode which is not driven and which is the other illumination mode.

The reporting unit 59 may output a report in real time from time T0 or output a report at a desired timing or for a desired period of time.

[Operating Method]

An example report of the operable time which is the driving capability will be explained with reference to FIGS. 4 and 5 below.

[Report of Operable Time for First Illumination Mode]

For example, the selection setting unit 21 selects and sets the first illumination mode and the maximum light amount state of the first illumination mode by the operation of the user at time T0 shown in FIG. 4. Time T shown in FIG. 4 is immediately after the operation starts, and the time when the first illumination mode is selected.

Next, the controller 23 controls the light source controller 25 based on the required consumption energy information (consumption electric power amount including the coefficient C1$a$) of the maximum light amount state of the first illumination mode stored in the first storage 41, and the driving state and driving condition of the maximum light amount state of the first illumination mode stored in the third storage 45 in accordance with the setting. The second storage 43 stores that the illumination mode is the maximum light amount state of the first illumination mode.

Next, the light source controller 25 controls the light sources 27$a$ and 27$b$ based on the control by the controller 23.

In the first illumination mode, the light source controller 25 only drives the light source 27$a$ so that the white light, in which blue laser beam and yellow fluorescence are mixed, is generated as illumination light, and the white light is emitted from the emitter 33.

The detector 53 detects a remaining capacity B1 at time T0 based on the change in voltage value of the supply source 51, when the maximum light amount state of the first illumination mode is selected, i.e., at time T0 shown in FIG. 4.

Next, the controller 23 transmits to the prediction calculation circuit 55 the required consumption energy information (coefficient C1$a$) of the maximum light amount state of the first illumination mode stored in the first storage 41.

Then, the prediction calculation circuit 55 calculates the capacity consumption predictive value in the maximum light amount state of the first illumination mode, based on the required consumption energy information (coefficient C1$a$) of the maximum light amount state of the first illumination mode transmitted from the controller 23, and the energy capacity consumption information (operable time) of the maximum light amount state of the first illumination mode stored in the first storage 41.

The capability calculation circuit 57 calculates the driving capability of the supply source 51 in the maximum light amount state of the first illumination mode, based on the remaining capacity B1 detected by the detector 53, and the capacity consumption predictive value of the maximum light amount state of the first illumination mode calculated by the prediction calculation circuit 55.

Then, the reporting unit 59 reports the operable time which is the driving capability at time T0, as shown in FIG. 5. The reporting unit 59 reports, for example, "the remaining operable time of the first illumination mode is 3 hours".

As explained above, in the present embodiment, the operable time of the maximum light amount state of the selected first illumination mode is reported immediately after operation starts.

The detector 53 may detects a remaining capacity B2 at time T1 shown in FIG. 4, based on the change in voltage value of the supply source 51, while the first illumination mode is driven. The prediction calculation circuit 55 may calculate the capacity consumption predictive value of the maximum light amount state of the first illumination mode based on the required consumption energy information (coefficient C1$a$) of the maximum light amount state of the first illumination mode at time T1 while the first illumination mode is driven. The capability calculation circuit 57 may calculate the driving capability of the supply source 51 corresponding to the first illumination mode, based on the remaining capacity B2 and the capacity consumption predictive value at time T1 shown in FIG. 4. As shown in FIG. 5, the reporting unit 59 may report the operable time of the maximum light amount state of the first illumination mode at time T1. The reporting unit 59 reports, for example, "the remaining operable time of the first illumination mode is 2 hours".

Accordingly, if the maximum light amount state of the first illumination mode continues operating with the required consumption energy information (coefficient C1$a$) of the maximum light amount state of the first illumination mode until time T1, the remaining capacity decreases in accordance with the required consumption energy information (coefficient C1$a$). At time T1, the operable time of the maximum light amount state of the first illumination mode may be reported, based on the remaining capacity B2 that decreased in accordance with the required consumption energy information (coefficient C1$a$), and the capacity consumption predictive value.

The reporting unit 59 may report the operable time updated at predetermined time intervals.

[Report of Operable Time for Second Illumination Mode]

For example, the selection setting unit 21 selects and sets the second illumination mode and the maximum light amount state of the second illumination mode by an operation of the user after time T2 shown in FIG. 4. By this operation, the illumination mode is switched to the maximum light amount state of the second illumination mode.

At time T2 when the illumination mode is switched, the second storage 43 stores the consumption energy information indicating the energy consumed in the maximum light amount state of the first illumination mode, and the operating time of the maximum light amount state of the first illumination mode that are associated with each other, as accumulated consumption energy information of the maximum light amount state of the first illumination mode. The second storage 43 performs the storing in accordance with switching of the illumination mode.

The controller 23 controls the light source controller 25 based on the required consumption energy information (consumption electric power amount including the coefficient C2$a$) of the maximum light amount state of the second illumination mode stored in the first storage 41, and the driving state and driving condition of the maximum light amount state of the second illumination mode stored in the third storage 45 in accordance with the setting. The second storage 43 stores that the illumination mode is the maximum light amount state of the first illumination mode.

The light source controller 25 controls the light sources 27$a$ and 27$b$ based on the control by the controller 23.

In the second illumination mode, the light source controller 25 only drives the light source 27$b$ so that mixed light, in which violet laser beam and green fluorescence are mixed, is generated as illumination light, and the mixed light is emitted from the emitter 33.

The detector 53 detects a remaining capacity B3 at time T2 based on the change in voltage value of the supply source 51, when the maximum light amount state of the second illumination mode is selected, i.e., at time T2 shown in FIG. 4.

Next, the controller 23 transmits to the prediction calculation circuit 55 the required consumption energy information (coefficient C2a) of the maximum light amount state of the second illumination mode stored in the first storage 41.

Then, the prediction calculation circuit 55 calculates the capacity consumption predictive value in the maximum light amount state of the second illumination mode, based on the required consumption energy information (coefficient C2a) of the maximum light amount state of the second illumination mode transmitted from the controller 23, and the energy capacity consumption information (operable time) of the maximum light amount state of the second illumination mode stored in the first storage 41.

The capability calculation circuit 57 calculates the driving capability of the supply source 51 in the maximum light amount state of the second illumination mode, based on the remaining capacity B3 detected by the detector 53, and the capacity consumption predictive value of the maximum light amount state of the second illumination mode calculated by the prediction calculation circuit 55.

Then, the reporting unit 59 reports the operable time which is the driving capability at time T2, as shown in FIG. 5. The reporting unit 59 reports, for example, "the remaining operable time of the second illumination mode is 3 hours".

As explained above, in the present embodiment, the prediction calculation circuit 55 calculates the capacity consumption predictive value corresponding to the switched second illumination mode immediately after the first illumination mode is switched to the second illumination mode. In addition, the reporting unit 59 reports the operable time of the maximum light amount state of the second illumination mode immediately after the first illumination mode is switched to the second illumination mode.

The detector 53 may detects a remaining capacity B4 at time T3 shown in FIG. 4, based on the change in voltage value of the supply source 51, while the second illumination mode is driven. The prediction calculation circuit 55 may calculate the capacity consumption predictive value of the maximum light amount state of the first illumination mode based on the required consumption energy information (coefficient C2a) of the maximum light amount state of the second illumination mode at time T3 while the second illumination mode is driven. The capability calculation circuit 57 may calculate the driving capability of the supply source 51 corresponding to the second illumination mode, based on the remaining capacity B4 and the capacity consumption predictive value at time T3 shown in FIG. 4. As shown in FIG. 5, the reporting unit 59 may report the operable time of the maximum light amount state of the second illumination mode at time T3. The reporting unit 59 reports, for example, "the remaining operable time of the second illumination mode is 2 hours".

Accordingly, if the maximum light amount state of the second illumination mode operates with the required consumption energy information (coefficient C2a) of the maximum light amount state of the second illumination mode until time T3, the remaining capacity decreases in accordance with the required consumption energy information (coefficient C2a). At time T3, the operable time of the maximum light amount state of the second illumination mode may be reported based on the remaining capacity B4 that decreased in accordance with the required consumption energy information (coefficient C2a) and the capacity consumption predictive value.

The reporting unit 59 may report the operable time updated at predetermined time intervals.

At time T4 when the illumination mode is switched to the stand-by state, the second storage 43 stores the consumption energy information indicating the energy consumed in the maximum light amount state of the second illumination mode, and the operating time of the maximum light amount state of the second illumination mode that are associated with each other as accumulated consumption energy information of the maximum light amount state of the second illumination mode.

[Report of Operable Time for Undriven First Illumination Mode while Second Illumination Mode is Driven]

The report of operable time for the undriven first illumination mode while the second illumination mode is driven will be explained below. This situation is illustrated as the period from time T2 to time T4 shown in FIG. 4.

In this case, the prediction calculation circuit 55 calculates the consumption energy information and the capacity consumption predictive value of the maximum light amount state of the first illumination mode, based on the accumulated consumption energy information of the maximum light amount state of the first illumination mode for the period from time T0 to time T2 stored in the second storage 43.

The capability calculation circuit 57 may calculate the driving capability of the supply source 51 corresponding to the undriven first illumination mode, based on the remaining capacities B3 and B4 and the capacity consumption predictive value.

As shown in FIG. 5, the reporting unit 59 reports the driving capability corresponding to the maximum light amount state of the undriven first illumination mode and calculated at the capability calculation circuit 57. The reporting unit 59 reports, for example, "the remaining operable time of the first illumination mode is 1 hour" at time T2, and "the remaining operable time of the first illumination mode is 40 minutes" at time T3. The reporting unit 59 reports the above at the same time as reporting the operable time of the second illumination mode.

[Report of Operable Time for First and Second Illumination Modes in Stand-by State]

At time T4, both the first and second illumination modes are not selected, and are in the stand-by state. The stand-by state may be set at a desirable timing after starting the operation, in accordance with the operation of the selection setting unit 21. The report of the operable time for the first and second illumination modes in the stand-by state will be explained below. In this case, the light sources 27a and 27b are stopped, for example.

The detector 53 detects a remaining capacity B5 at time T4 shown in FIG. 4, based on the change in voltage value of the supply source 51.

Next, the controller 23 sends to the prediction calculation circuit 55 the accumulated consumption energy information of the maximum light amount state of the first illumination mode for the period from time T0 to time T2, and the accumulated consumption energy information of the maximum light amount state of the second illumination mode for the period from time T2 to time T4, that are stored in the second storage 43.

In this case, the prediction calculation circuit 55 calculates the consumption energy information and the capacity consumption predictive value of the maximum light amount state of the first illumination mode, based on the accumulated consumption energy information of the maximum light amount state of the first illumination mode for the period from time T0 to time T2 stored in the second storage 43.

Then, the capability calculation circuit 57 calculates the driving capability of the supply source 51 corresponding to the maximum light amount state of the undriven first illumination mode, based on the remaining capacity B5 and the capacity consumption predictive value during the stand-by state.

As shown in FIG. 5, the reporting unit 59 reports the driving capability corresponding to the maximum light amount state of the undriven first illumination mode and calculated at the capability calculation circuit 57.

Similarly, the prediction calculation circuit 55 calculates the consumption energy information and the capacity consumption predictive value of the maximum light amount state of the second illumination mode, based on the accumulated consumption energy information of the maximum light amount state of the second illumination mode for the period from time T2 to time T4 stored in the second storage 43.

Then, the capability calculation circuit 57 calculates the driving capability of the supply source 51 corresponding to the maximum light amount state of the undriven second illumination mode, based on the remaining capacity B5 and the capacity consumption predictive value during the stand-by state.

As shown in FIG. 5, the reporting unit 59 reports the driving capability corresponding to the maximum light amount state of the undriven second illumination mode and calculated at the capability calculation circuit 57.

By the above processing, the reporting unit 59 reports, for example, "the remaining operable time of the first illumination mode is 20 minutes" and "the remaining operable time of the second illumination mode is 1 hour", at the same time.

[Advantageous Effects]

As explained above, in the present embodiment, one of the plurality of illumination modes is selectable, and the driving capability (operable time) of the supply source 51 corresponding to the set illumination mode can be reported to the user. Accordingly, in the present embodiment, the user can easily ascertain the operable time for the current illumination mode. Thus, in the present embodiment, by such ascertainment, it is possible to prevent adverse effects on usage due to a stoppage of illumination light emission.

In the present embodiment, in the situation where the first illumination mode which is different from the currently driven second illumination mode is not driven, if the first illumination mode was previously driven, the driving capability (operable time) of the supply source 51 in the first illumination mode can be reported to the user, based on the accumulated consumption energy information for the time when the first illumination mode was driven, even though the second illumination mode is currently used.

In the present embodiment, in the stand-by state, the operable time for each illumination mode relative to the current remaining capacity can be easily obtained so that the user can use each illumination mode in consideration of selection of an effective illumination mode relative to the remaining capacity and selection time.

Figure 6:
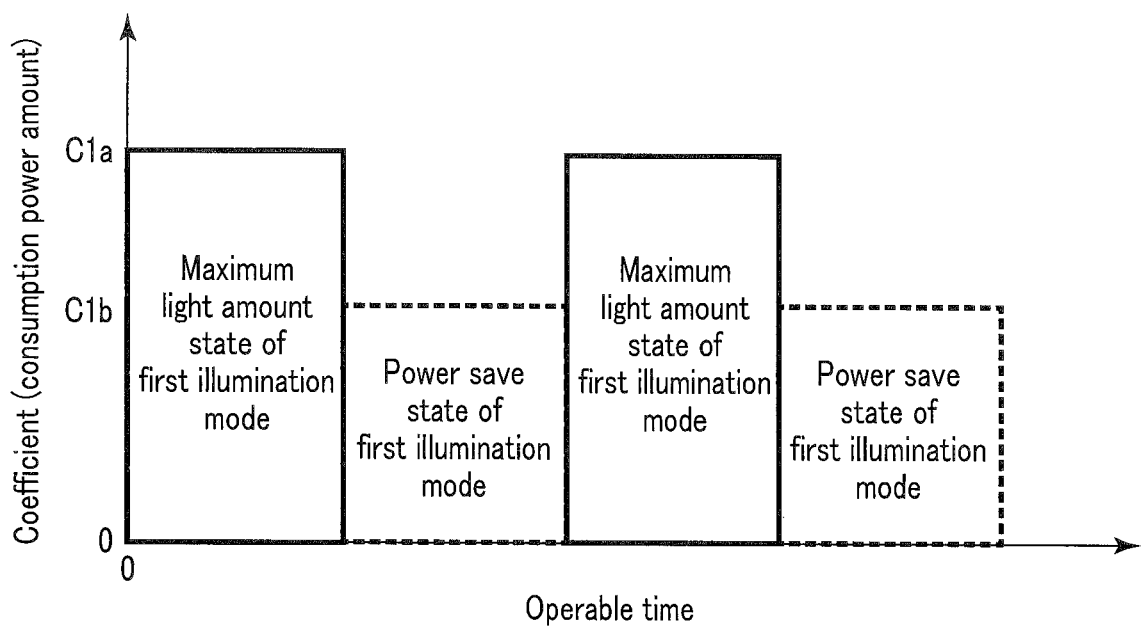
FIG. 6 illustrates coefficients for each state of the first illumination mode.

In the present embodiment, the light source controller 25 controls the energy amount in each state, i.e., the consumption electric power amount having coefficients shown in FIG. 6. Accordingly, the light source 27a, for example, emits white light having the light amount varying in accordance with the values of the driving current, such as the maximum light amount state, the electric power save state, and the average light amount state. Therefore, in the present embodiment, the operable time can be reported for each state, and the user can obtain the light amount values and the operable time for each state of the illumination mode of the same emitted light color.

Second Embodiment

In the first embodiment, the light source controller 25 switches a destination of energy supply in accordance with the illumination mode. However, if respective illumination modes can emit illumination light of different light emission spectra, the light source controller 25 is not limited to perform such switch processing.

For example, the light source controller 25 may control the ratio of driving current which is the ration of energy supply, in accordance with the illumination mode so that the light sources 27a and 27b are simultaneously driven in the state where the driving ratio of energy is different in accordance with the illumination mode.

Figure 7:
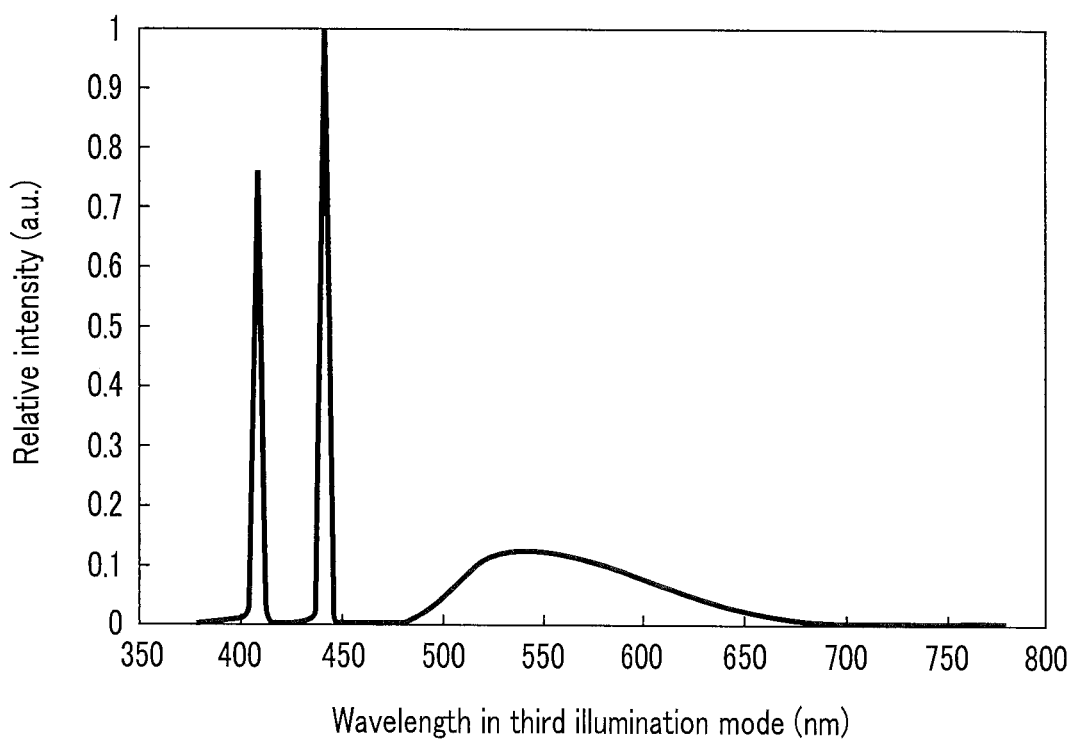
FIG. 7 illustrates a light emission peak intensity in a third illumination mode in a second embodiment.

FIG. 7 illustrates a light emission peak intensity in a third illumination mode where the light sources 27a and 27b are simultaneously driven in the present embodiment.

In the present embodiment, the prediction calculation circuit 55 calculates the energy capacity consumption information based on the required consumption energy information in accordance with the ratio of driving current. The capability calculation circuit 57 calculates the driving capability based on the energy capacity consumption information.

In the present embodiment, the operable time is accurately reported even in the illumination mode where the plurality of light sources 27a and 27b are simultaneously used to emit multiple illumination light.

Third Embodiment

Figure 8:
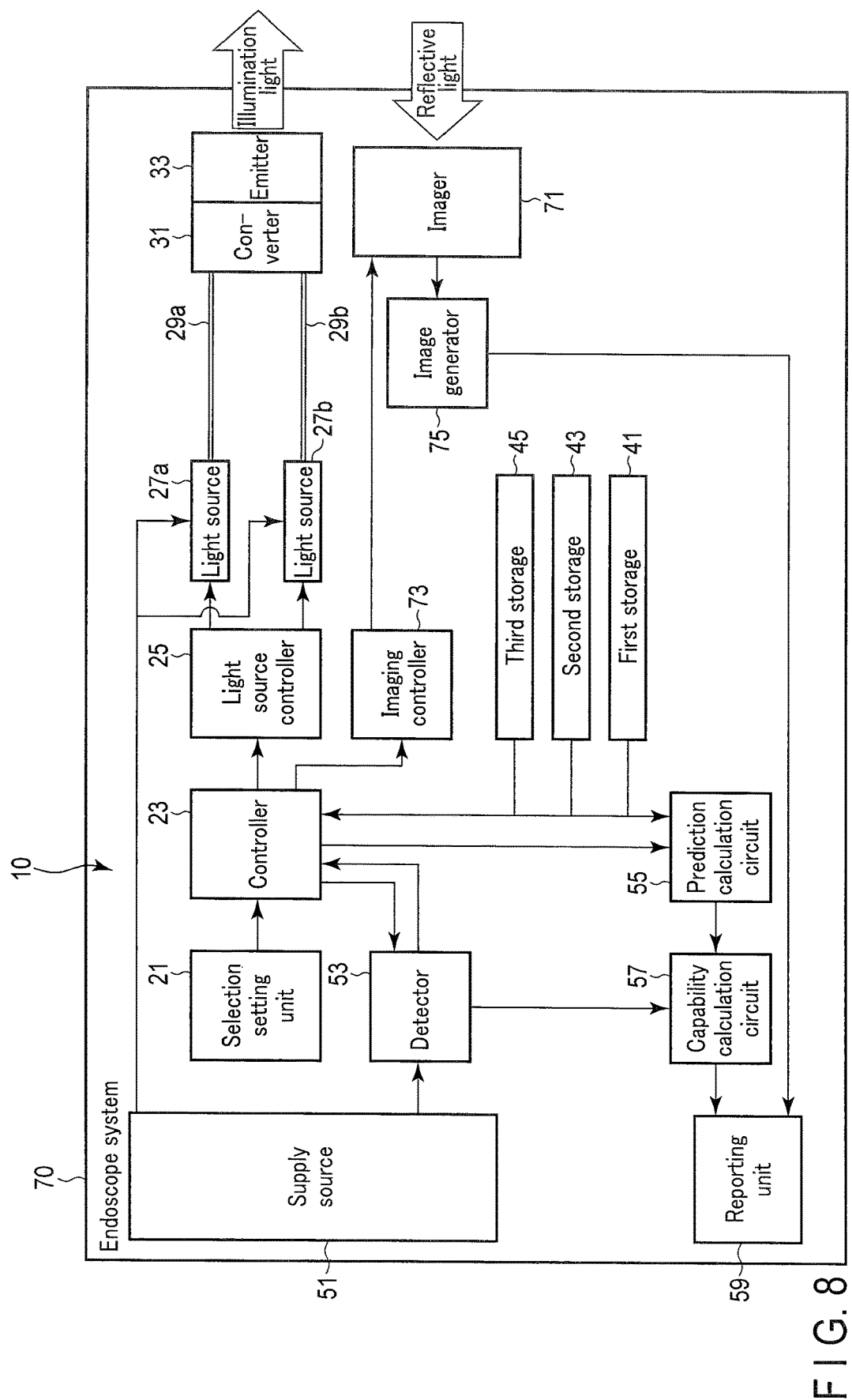
FIG. 8 is a schematic diagram of an endoscope system having an endoscope light source device according to a third embodiment.

With reference to FIG. 8, the parts different from the first embodiment will be explained below.

In the first embodiment, the operable time for each illumination mode is reported; however, the report is not limited thereto. The operable time according to an observation mode may be reported. Accordingly, in the present embodiment, an endoscope system 70 includes a plurality of observation modes. The observation modes are selected and set by a selection setting unit 21.

The endoscope system 70 further includes a light source device 10, an imager (imaging unit) 71 that images a subject in each observation mode based on a reflective light from the subject when illumination light is applied to the subject in each illumination mode, an imaging controller (imaging control unit) 73 that controls the imager 71, and an image generator (image generation unit) 75 that generates an image of the subject imaged by the imager 71.

The illumination mode in each element explained in the first embodiment can be replaced with the observation mode as indicated below. In the following descriptions, only part of each element will be explained for simplification.

In a first storage 41, required consumption energy information includes a consumption energy amount required for driving in each observation mode.

In the first storage 41, energy capacity consumption information includes the ratio of consuming the capacity of the supply source 51 by energy for each observation mode.

In a second storage 43, the accumulated consumption energy information is obtained by associating the consumption energy information indicating the consumed energy in each observation mode with the operable time for each observation mode, and indicates the energy amount (electric power amount) which is the amount of accumulated actual consumed energy in each observation mode.

A third storage 45 stores the driving state that indicates how the image generator 75 drives in each observation mode.

A prediction calculation circuit 55 calculates a capacity consumption predictive value indicating a ratio of consuming the capacity of the supply source 51 within a predetermined period of time in each observation mode, based on the consumption energy information.

A capability calculation circuit 57 calculates the driving capability of the supply source 51 corresponding to each observation mode, based on the remaining capacity and the capacity consumption predictive value.

A reporting unit 59 reports the driving capability. The reporting unit 59 displays an observation image in each observation mode.

In the aforementioned explanation, the illumination mode in each element explained in the first embodiment is replaced with the observation mode, but the mode is not limited thereto. The illumination mode in each element explained in the first embodiment can be replaced with an aspect including the illumination mode and the observation mode.

As stated above, the third embodiment can produce the same effect in the observation mode as in the illumination mode of the first embodiment.

It is to be noted that the present invention is not limited to the above-described embodiment, and can be provided by modifying the constituent elements in the embodiment stages without departing from the gist of the invention. By appropriately combining the plurality of constituent features disclosed in the embodiments, various inventions may be formed.

What is claimed is:

1. An endoscope light source device comprising:
a light source configured to be driven by energy supplied from a supply source, and to be operable to switch between a plurality of illumination modes, wherein each of the plurality of illumination modes has at least a first state and a second state; and
a processor comprising hardware, wherein the processor is configured to:
select and set one of the illumination modes and the first state or the second state;
control a storage to store each illumination mode and each of the first and second states in association with a consumption energy amount;
detect a remaining capacity of the supply source based on a voltage value that changes in accordance with a change in a remaining capacity of the supply source immediately before driving the selected illumination mode in the set state or during driving the selected illumination mode in the set state or based on an accumulated amount of consumed energy;
calculate a capacity consumption predictive value indicating a ratio of consuming a capacity of the supply source within a predetermined period of time in each of the illumination modes read from the storage, based on required consumption energy information that indicates a consumption energy amount required for driving each of the illumination modes;
calculate a driving capability of the supply source corresponding to each of the illumination modes, based on the remaining capacity and the capacity consumption predictive value; and
control an output device to, when switching between the illumination modes, report the driving capability of the supply source of each of an illumination mode before the switching and an illumination mode after the switching selectively by display or vibration.

2. The endoscope light source device according to claim 1, wherein the processor is configured to, when a first illumination mode of the illumination modes is switched to a second illumination mode of the illumination modes, calculate the capacity consumption predictive value corresponding to the second illumination mode.

3. The endoscope light source device according to claim 2,
wherein the processor is configured to:
calculate the capacity consumption predictive value of the first illumination mode, based on the required consumption energy information of the first illumination mode immediately before the energy is supplied from the supply source in the first illumination mode; and
calculate the capacity consumption predictive value of the second illumination mode, based on the required consumption energy information of the second illumination mode which is different from the required consumption energy information of the first illumination mode immediately before the energy is supplied from the supply source in the second illumination mode.

4. The endoscope light source device according to claim 3,
wherein the processor is configured to, immediately before the first illumination mode is switched to the second illumination mode and the energy is supplied from the supply source in the second illumination mode, calculate the driving capability of the supply source corresponding to the first illumination mode, and control the output device to report the driving capability of the supply source corresponding to the first illumination mode.

5. The endoscope light source device according to claim 4,
wherein, the processor is configured to, when the illumination modes are in a stand-by state, calculate the driving capability corresponding to each illumination mode, and control the output device to simultaneously report the driving capability for each illumination mode.

6. The endoscope light source device according to claim 3,
wherein the processor is configured to:
control the storage to store the required consumption energy information including a coefficient, and energy capacity consumption information indicating a ratio of consuming the capacity of the supply source by the energy for each illumination mode; and
calculate the capacity consumption predictive value, based on the required consumption energy information and the energy capacity consumption information.

7. The endoscope light source device according to claim 6,
wherein the processor is configured to calculate an operable time included in the driving capability and indicating a time duration where each of the illumination modes is continuously usable relative to the remaining capacity.

8. The endoscope light source device according to claim 6,
wherein the processor is configured to calculate a ratio of the remaining capacity to a full capacity, based on the remaining capacity and the capacity consumption predictive value.

9. The endoscope light source device according to claim 3,
wherein the processor is configured to, immediately before the first illumination mode is switched to the second illumination mode and the energy is supplied from the supply source in the second illumination mode, calculate the required consumption energy information of the one of the illumination modes based on accumulated consumption energy information of the one of the illumination modes that indicates an energy amount that the one of the illumination modes actually consumed, and calculate the capacity consumption predictive value of the one of the illumination modes.

10. The endoscope light source device according to claim 1,
wherein the light source comprises:
a first light source configured to emit light having a desired light emission peak intensity in a first wavelength region; and
a second light source configured to emit light having a desired light emission peak intensity in a second wavelength region which is different from the first wavelength region, and
wherein the processor is configured to:
switch a destination of energy supply in accordance with the illumination modes so that the first light source and the second light source are independently driven in accordance with the illumination modes,
wherein each of the illumination modes emits illumination light having a different light emission spectrum by control of the processor.

11. The endoscope light source device according to claim 1,
wherein the light source comprises:
a first light source configured to emit light having a desired light emission peak intensity in a first wavelength region; and
a second light source configured to emit light having a desired light emission peak intensity in a second wavelength region which is different from the first wavelength region, and
wherein the processor is configured to:
control a ratio of energy supply in accordance with the illumination modes so that the first light source and the second light source are simultaneously driven with different energy driving ratios in accordance with the illumination modes,
wherein each of the illumination modes emits illumination light having a different light emission spectrum by control of the processor.

12. The endoscope light source device according to claim 10,
wherein the processor is configured to control an amount of the energy to be supplied.

13. The endoscope light source device according to claim 11,
wherein the processor is configured to control an amount of the energy to be supplied.

14. The endoscope light source device according to claim 1, wherein the processor is configured to detect a difference between an initial value of a capacity of the supply source and accumulated consumption energy information as the remaining capacity.

15. The endoscope light source device according to claim 1, wherein the processor is configured to detect the remaining capacity based on a voltage value of the supply source which varies in accordance with a change in the remaining capacity.

16. The endoscope light source device according to claim 1, further comprising the supply source.

* * * * *